(12) United States Patent
Geddes et al.

(10) Patent No.: US 7,014,611 B1
(45) Date of Patent: Mar. 21, 2006

(54) OSCILLOMETRIC NONINVASIVE BLOOD PRESSURE MONITOR

(75) Inventors: Leslie A. Geddes, Lafayette, IN (US); Rebecca A. Roeder, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/876,308

(22) Filed: Jun. 24, 2004

(51) Int. Cl.
*A61B 5/02* (2006.01)

(52) U.S. Cl. ............... 600/490; 600/494; 600/495; 600/493

(58) Field of Classification Search ........ 600/490–503, 600/481, 483, 484, 485
See application file for complete search history.

(56) References Cited

U.S. PATENT DOCUMENTS

| | | | | |
|---|---|---|---|---|
| 4,469,107 A | * | 9/1984 | Asmar et al. | 600/494 |
| 4,754,406 A | * | 6/1988 | Miyawaki et al. | 600/493 |
| 5,261,414 A | * | 11/1993 | Aung et al. | 600/496 |
| 5,368,039 A | * | 11/1994 | Moses | 600/494 |
| 6,801,798 B1 | * | 10/2004 | Geddes et al. | 600/323 |

* cited by examiner

*Primary Examiner*—Max F. Hindenburg
*Assistant Examiner*—Navin Natnithithadha
(74) *Attorney, Agent, or Firm*—William F. Bahret

(57) ABSTRACT

An oscillometric, noninvasive blood pressure monitor comprising an inflatable cuff adapted for placement around a body member, a pump for cuff inflation, a pressure transducer connected to the cuff, means for detecting oscillations in arterial pressure occurring during a transition in cuff pressure between a pressure greater than normal systolic pressure and a pressure less than normal diastolic pressure, and a blood pressure measurement circuit which is capable of determining the maximum amplitude ($A_m$) of the oscillations, identifying mean cuff pressure ($P_m$) as the coincident value of the cuff-pressure signal from the pressure transducer, and determining systolic pressure as a function of both $A_m$ and $P_m$. In accordance with one aspect of the invention, the blood pressure monitor has an optical sensor including a light source and photodetector optically coupled to the body member proximate to the cuff. Oscillations in the output signal of the photodetector are detected, and the blood pressure measurement circuit determines the oscillation amplitude corresponding to systolic pressure ($A_s$) as a function of both $A_m$ and $P_m$.

18 Claims, 3 Drawing Sheets

OSCILLOMETRIC NONINVASIVE BLOOD PRESSURE MONITOR

BACKGROUND OF THE INVENTION

This invention relates to the noninvasive measurement of blood pressure, and more particularly to the noninvasive measurement of blood pressure by the oscillometric method.

A number of noninvasive methods of measuring blood parameters are known. For example, blood pressure has been measured by the auscultatory method which uses a cuff and a stethoscope, and by the oscillometric method which only requires a cuff applied to a body member. The conventional oscillometric method relies on the small-amplitude pulsatile pressure oscillations communicated to the cuff by the underlying artery in the body member during cuff deflation from above systolic pressure to zero pressure. Such arterial pressure oscillations cause corresponding small oscillations in cuff pressure which can be amplified and used to identify systolic, mean and diastolic pressure. For example, it has been established by Posey et al. that the cuff pressure for maximal amplitude oscillations corresponds to mean arterial pressure. See Posey et al., "The Meaning of the Point of Maximum Oscillations in Cuff Pressure in the Direct Measurement of Blood Pressure," Part 1, *Cardiovascular Res. Ctr. Bull.* 8(1):15–25, 1969. See also Ramsey, "Noninvasive Automatic Determination of Mean Arterial Pressure," *Med. Biol. Eng. Comput.* 17:17–18, 1979; and Geddes et al., "Characterization of the Oscillometric Method for Measuring Indirect Blood Pressure," *Annals of Biomedical Engineering, Vol.* 10, pp. 271–280, 1982. All such references are incorporated herein by reference.

Commercially available oscillometric devices are useful for noninvasive blood pressure measurement, but a need remains for improvement in accuracy, particularly with respect to identification of systolic and diastolic pressure.

SUMMARY OF THE INVENTION

The present invention meets the above-stated need and others by providing an oscillometric, noninvasive blood pressure monitor comprising an inflatable cuff adapted for placement around a body member, a pump for cuff inflation, a pressure transducer connected to the cuff, means for detecting oscillations in arterial pressure occurring during a transition in cuff pressure between a pressure greater than normal systolic pressure and a pressure less than normal diastolic pressure, and a blood pressure measurement circuit which is capable of determining the maximum amplitude ($A_m$) of the oscillations, identifying mean cuff pressure ($P_m$) as the coincident value of the cuff-pressure signal from the pressure transducer, and determining systolic pressure as a function of both $A_m$ and $P_m$. An inflatable cuff as that term is used herein is an inflatable bladder, capsule or other member suitable for occluding a blood vessel, and may cover a small area on a subject's skin or may surround a finger, limb or other body part.

In accordance with one aspect of the invention, the blood pressure monitor has an optical sensor including a light source and photodetector optically coupled to the body member through at least one surface of the cuff. The oscillations in arterial pressure are detected as oscillations in the output signal of the photodetector, and the blood pressure measurement circuit determines the oscillation amplitude corresponding to systolic pressure ($A_s$) as a function of both $A_m$ and $P_m$. In a preferred embodiment, the amplitude $A_s$ corresponding to systolic pressure is determined based on an equation of the form $$A_s = A_m(a - b\, P_m)$$

The invention provides more accurate blood pressure measurement by determining systolic pressure according to an algorithm which includes mean cuff pressure as a factor. The principles of the invention are particularly suited for use with the optical oscillometric method but are equally applicable to blood pressure measurement by the conventional pneumatic oscillometric method.

The objects and advantages of the present invention will be more apparent upon reading the following detailed description in conjunction with the accompanying drawings.

DETAILED DESCRIPTION OF THE PREFERRED EMBODIMENTS

Figure 1:
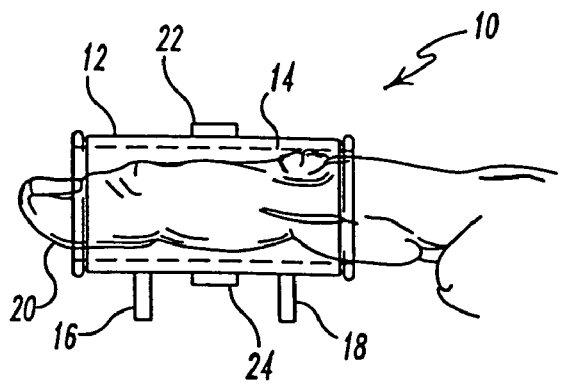
FIG. 1 is a side view of a cylindrical embodiment of a transilluminating cuff for use in a blood pressure monitor according to the present invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one of ordinary skill in the art to which the invention relates.

FIG. 1 illustrates one embodiment of a member-transilluminating, transparent pressurizable cuff 10 for use in a blood pressure monitor according to the present invention. A rigid tube 12 contains an elastic sleeve 14 which may be provided with an inlet 16 for connection to a pressure source, e.g., an air supply, and an outlet 18 for connection to, e.g., a manometer. Alternatively, inlet 16 may be the only pressure line, as in the embodiment of FIG. 2 described below. Pressure applied between the elastic sleeve and the rigid tube causes the sleeve to compress a body member therein such as a finger 20 placed therein. This embodiment is also useful on a small animal tail or tongue, for example, among other applications. The rigid tube includes a light source 22 and a photodetector 24 which may be diametrically opposed as illustrated in the drawing. Alternatively, two light sources may be provided as described below. In another alternative embodiment, the light source and photodetector are mounted side-by-side on the cuff housing, and blood pressure and oxygen saturation are measured based on reflection of light by tissue in the body member.

Figure 2:
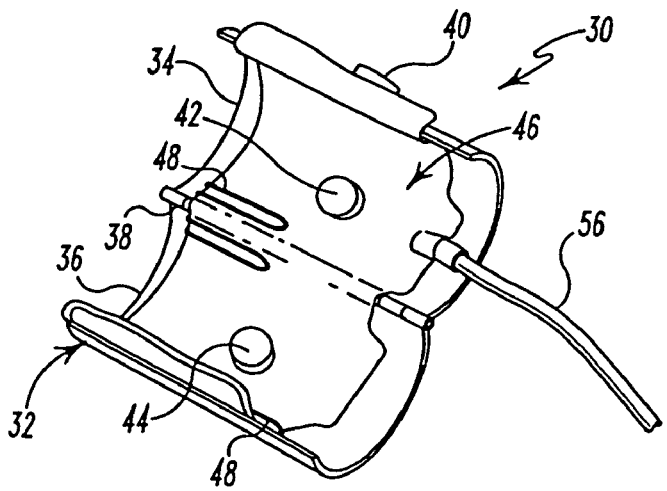
FIG. 2 is a perspective view of a hinged embodiment of a transilluminating pressure cuff.
Figure 3:
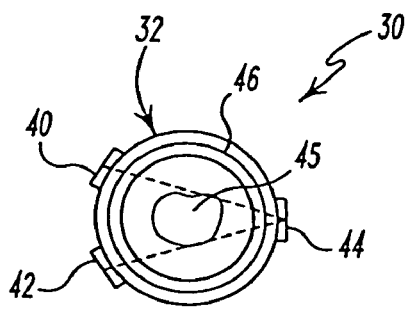
FIG. 3 is a transverse cross-section of the cuff of FIG. 2.

Referring to FIGS. 2 and 3, another embodiment of a cuff 30 for use with a blood pressure monitor according to the present invention includes a hinged cuff housing 32 having first and second semicylindrical sections 34 and 36 and a hinge 38 parallel to the longitudinal axis of the semicylindrical housing sections. The axes of the two housing sections are parallel to each other and coincide to form a common axis when the hinged housing is closed. In order to facilitate use of the cuff on a bone-containing body member, i.e., to avoid bone shadow, two light sources 40 and 42 are circumferentially spaced on one housing section in opposition to a photodetector 44 mounted on the other housing section. This configuration increases the transmission of light through the tissue bed around the bone 45 in the member in which blood pressure is measured noninvasively. The angular spacing of the LEDs and the photodetector may be as shown in FIG. 3, or, alternatively, the LEDs and photodetector may be spaced approximately 120° apart. An optically transparent, inflatable cuff 46, which may be provided as a disposable item with an inflation tube 56, is adapted to fit within cuff housing 32 and around the body member, and is held in place by means of a plurality of clips 48 which are provided in the housing for this purpose. Cuff 30 is further described in U.S. Pat. No. 6,801,798, entitled Body-Member-Illuminating Pressure Cuff For Use In Optical Noninvasive Measurement Of Blood Parameters, issued Oct. 5, 2004 and hereby incorporated by reference.

Blood pressure, including systolic, mean and diastolic pressures, can be obtained with the optical sensor unit from the amplitude spectrum of the pulses obtained during deflation of the cuff from a suprasystolic pressure to zero pressure, as described below. Monochromatic LEDs are suitable for monitoring blood pressure. For example, the transducer may employ infrared LEDs such as PDI-E801 or PDI-E804 880 nm LEDs available from Photonic Detectors, Inc. The LEDs and photodetector are preferably matched to operate at a desired wavelength. One example of a suitable photodetector is a Fairchild Semiconductor QSD723 phototransistor, with a peak sensitivity at 880 nm. Another suitable operating wavelength for the LEDs and photodetector is 805 nm, at which wavelength the blood pressure pickup has no oxygen-saturation error, as will be appreciated from the discussion of pulse oximetry below. An advantage of either of the example wavelengths is that there are few environmental light sources in this infrared region.

Figure 4:
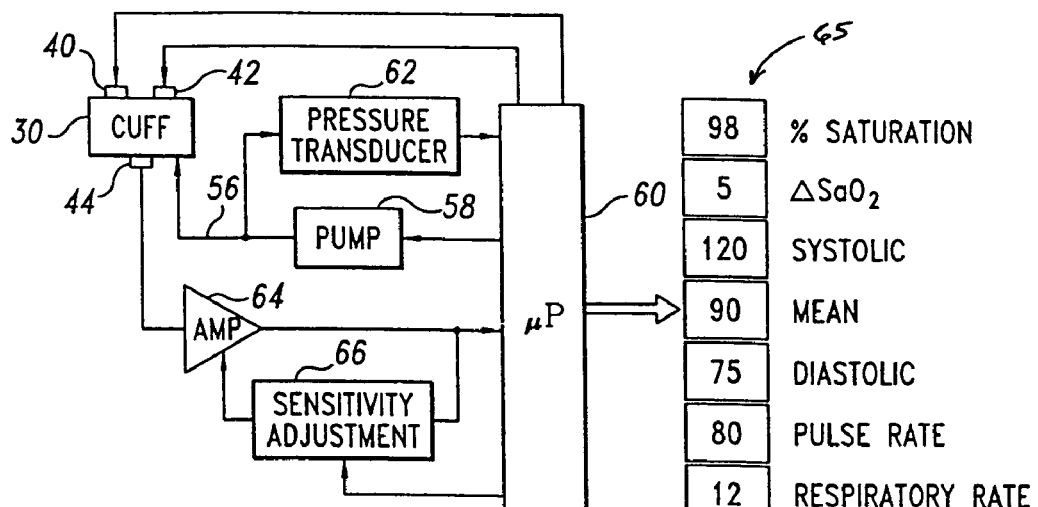
FIG. 4 is a block diagram of one embodiment of a blood pressure monitor according to the present invention.

Referring to FIG. 4, the cuff is connected by inflation tube 56 to a pump 58 which is controlled by a microprocessor 60. Pressure in the line to the cuff is measured by means of a pressure transducer 62 having a signal output connected to the microprocessor. Suitable transducers are available from Cobe Labs, Littleton, Colo. In embodiments such as that of FIG. 1 in which the cuff has an inlet and an outlet, the pressure transducer is connected to the outlet. A/D conversion may be provided in the microprocessor or in the transducer or with a separate A/D converter provided between the two. The microprocessor controls the LEDs and, during blood pressure measurement, energizes both LEDs continually. The photodetector produces an output signal which is supplied to the microprocessor through an amplifier 64. The amplified photodetector output signal is converted to digital form in the microprocessor itself if the microprocessor has an internal A/D converter, or in a separate A/D converter provided between the amplifier and the microprocessor.

The microprocessor is suitably programmed to identify, based on the digitized output signal of the photodetector, the points in the cuff pressure signal which correspond to systolic, mean and diastolic pressure, and displays the corresponding values on a display 65 which may comprise separate indicators as shown in FIG. 4, or may provide an output for distant recording.

One suitable embodiment of amplifier 64 is a variable-gain amplifier. With such an amplifier, and with a feedback circuit 66 connected to its gain-control input, as shown in FIG. 4, the sensitivity of the measuring system may be adjusted automatically to a proper level for measurement of blood pressure. It has been found useful to set the sensitivity based on the amplitude of the photodetector output pulses before inflation of the cuff. Such pulses may have a peak-to-peak amplitude on the order of one-third to one-half the maximum peak-to-peak amplitude of the pulses obtained during blood pressure measurement. Such pulses are identified by the reference numeral 68 in FIG. 6, which shows a sample waveform for the photodetector output signal both prior to and during blood pressure measurement. Sensitivity adjustment is inhibited when blood pressure is measured. That is, the gain of amplifier 64 and thus the system sensitivity is fixed at that time. It should be noted that pulse rate can be determined from the optical pulses occurring before cuff inflation and after cuff deflation and may be displayed along with blood pressure values as indicated in FIG. 4.

Figure 5:
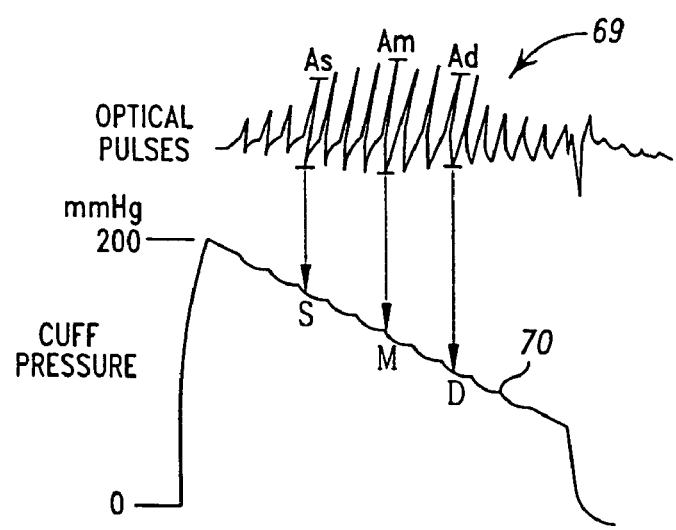
FIG. 5 is a set of sample waveforms obtained with a blood pressure monitor according to the present invention, with a cuff on the little finger of a human subject.

Blood pressure is measured during a transition in cuff pressure between a suprasystolic pressure and zero pressure. The transition may be an upward or downward transition but is described below in terms of a gradual downward transition such as shown in FIG. 5, which shows a sample optical pulse waveform 69 obtained during a cuff pressure cycle represented by curve 70, which is marked to indicate the points corresponding to systolic (S), mean (M), and diastolic (D) pressure. When cuff pressure is raised above systolic pressure, all oscillations are extremely small. As pressure in the cuff falls below systolic pressure, the pulses increase, and as the pressure is reduced further, the optical pulse amplitude increases and reaches a maximum, labeled $A_m$ in FIG. 5, at which point the cuff pressure is equal to mean arterial pressure, labeled M in FIG. 5. With a continued decrease in cuff pressure, the oscillation amplitude decreases and returns to a uniform level.

The peak-to-peak amplitudes of the optical pulse waveform at the points coinciding with the occurrence of systolic and diastolic pressure are designated respectively as $A_s$ and $A_d$ in FIG. 5. In the system described in the above-referenced U.S. Pat. No. 6,801,798, those amplitudes are calculated as fixed percentages of $A_m$, and the corresponding points in time are identified on the optical pulse waveform, by interpolation if necessary between adjacent pulses, after which the values of cuff pressure at those points in time are identified as systolic (S) and diastolic (D) pressure, respectively. Appropriate ratios have been determined experimentally. With a conventional cuff applied to the upper arm of a human subject, and with the cuff width (axial length) nominally equal to 40% of the member circumference, systolic pressure is typically identified as the value of cuff pressure at the point when the amplitude ratio $A_s/A_m$ is 0.5; diastolic pressure is typically identified as the value of cuff pressure at the point when the ratio of $A_d/A_m$ equals 0.8. With the optical oscillometric method, a ratio of 0.7 has been found more suitable for identifying diastolic pressure.

Systolic pressure, however, is preferably not identified on the basis of a fixed percentage of $A_m$. The amplitude of the optical pulse waveform corresponding to systolic pressure has been found to depend on mean pressure ($P_m$), unlike the fixed-value systolic pressure algorithm. More accurate measurements can be obtained by calculating $A_s$, the optical pulse amplitude corresponding in time with systolic pressure, according to an algorithm which includes mean cuff pressure as a factor. The following equation represents one form of such an algorithm:

$$A_s = A_m(a - b\, P_m)$$

where a and b are experimentally determined constants.

Figure 7:
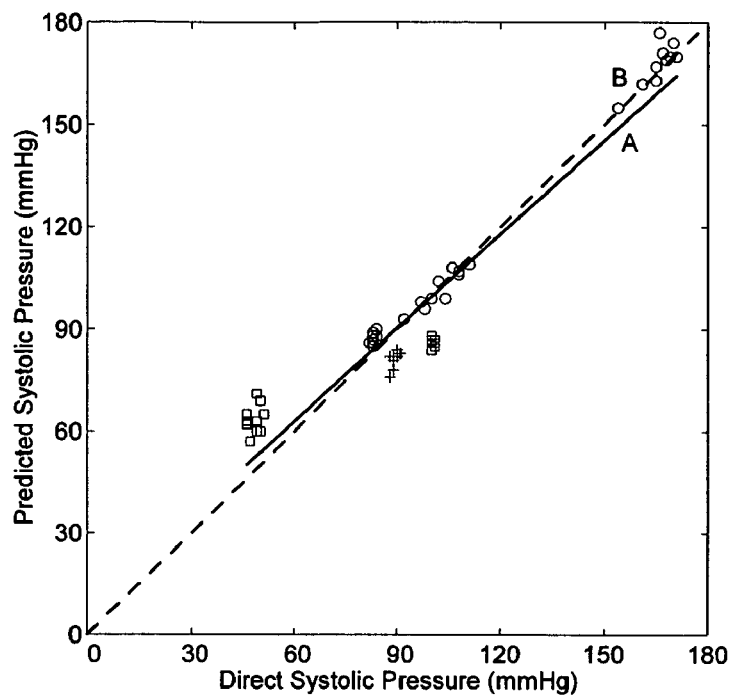
FIG. 7 is a graph of blood pressure measured using an algorithm according to the present invention against blood pressure measured directly.

The improvement in predicting systolic pressure using this algorithm can be appreciated from FIG. 7, in which line A, corresponding to results using this algorithm with the values a and b set equal to 0.84 and 0.004, respectively, is virtually coincident with line B, the line of equal values in the graph. That is, systolic pressure predicted with the above algorithm is virtually the same as directly measured systolic pressure throughout the range of interest.

Figure 6:
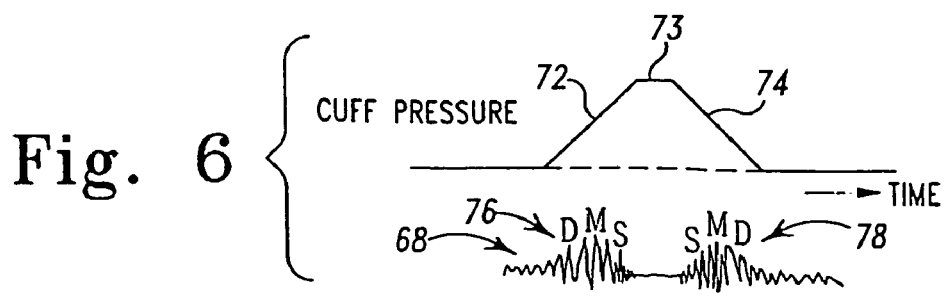
FIG. 6 is another set of sample waveforms.

FIG. 6 illustrates sample waveforms for an embodiment of the invention in which cuff pressure is increased linearly and then decreased linearly, as illustrated respectively by segments 72 and 74 of the cuff pressure signal, and two sets of optical pulsatile data 76 and 78 are acquired. As shown in the drawings, the first set of pulses 76 includes indications of the points in time during the cuff pressure rise 72 at which diastolic, mean and systolic pressure occur, in that order. Conversely, the second set of pulses 78 includes indications of the points in time during the cuff pressure fall 74 at which systolic, mean and diastolic pressure occur, in that order. In this way, two values for each pressure may be acquired and averaged and the average value may be displayed.

The system may have LEDs which operate at different wavelengths for oxygen saturation measurement. Blood oxygen saturation is defined as the ratio of oxygenated hemoglobin ($HbO_2$) to the total hemoglobin ($Hb+HbO_2$), and is typically expressed as a percentage. The oximeter determines oxygen saturation ($SaO_2$) by measuring the optical transmission at two wavelengths of light passing through a tissue bed. Although other wavelengths are contemplated, it is presently preferred to operate at wavelengths of approximately 650 nm and 805 nm for oxygen saturation measurement. As shown in the above-referenced U.S. Pat. No. 6,801,798, hemoglobin (Hb) has negligible transmission at 650 nm, and hemoglobin (Hb) and oxygenated hemoglobin ($HbO_2$) transmit equally well at 805 nm; the latter wavelength is known as the isobestic point. That is, the transmission at 805 nm is independent of oxygen saturation. The optical sensor may have separate narrowband LEDs, e.g., a red LED emitting at approximately 650 nm and an infrared LED preferably emitting at approximately 805 nm, and a broadband photodetector. As an alternative to separate narrowband LEDs, a red LED and infrared LED may be combined in one multi-wavelength LED such as type Epitex L660/805/975-40D00, available from Epitex, Kyoto, Japan, and each light source 40 and 42 may comprise such a multi-wavelength LED.

The red and infrared LEDs are preferably energized alternately in rapid succession, e.g., at a rate of 200 pulses per second. This technique permits the use of high-intensity short-duration pulses. Synchronous detection is used to achieve the highest signal-to-noise ratio. Two benefits result: 1) a low average power and minimum heating, and 2) the system is less sensitive to stray ambient illumination. The red and infrared signals are sampled and processed to obtain $SaO_2$, which may then be displayed on display 65 of FIG. 4. The automatic sensitivity adjustment is disabled during measurement of oxygen saturation.

A base line for measurement may be established by first inflating the cuff to a high pressure sufficient to squeeze all of the blood out of the member in the cuff and thus out of the optical path. For example, the cuff pressure may be held at a maximum pressure as indicated by the plateau 73 in FIG. 6 for a desired time period to obtain the bloodless transmission reading, which can be assigned a value of 100% transmission. When the cuff pressure is released, blood enters the optical path and the red and infrared transmissions are measured. The optical density is computed for each of the transmitted signals, and the ratio of red to infrared optical density is calculated and scaled to provide an output value corresponding to the percentage of oxygen saturation.

Figure 8:
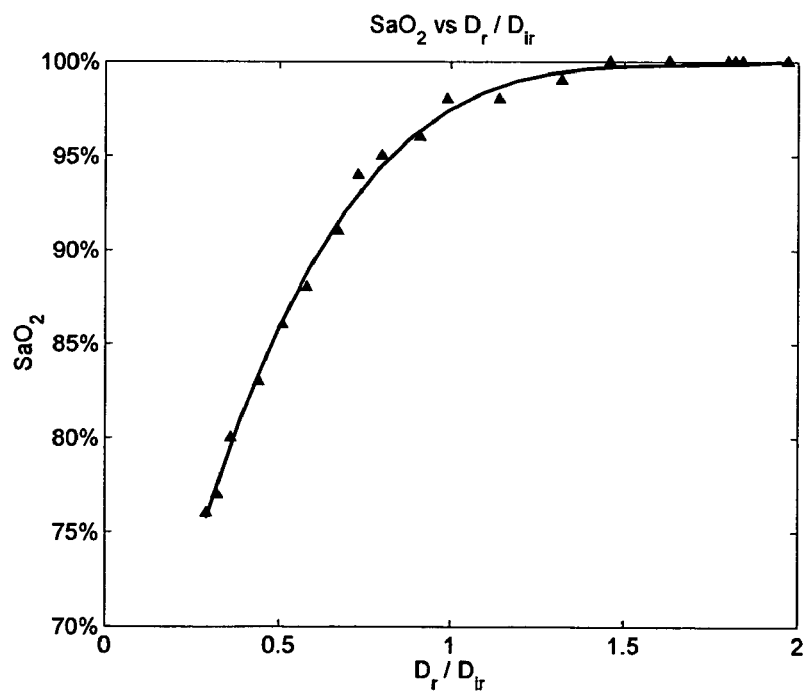
FIG. 8 is an example of a calibration curve for use in oxygen saturation measurement according to another embodiment the present invention.

Beer's law relates the optical density (D) to the concentration of a dissolved substance. Optical density (D) is equal to log 1/T, where T is the transmittance. Therefore the oxygen saturation ($SaO_2$) is given by:

$$SaO_2 = A\frac{D_{650}}{D_{805}} + B$$

where A and B are experimentally determined constants for a given application. This equation predicts a linear relationship based on Beer's law. However, Beer's law applies to solutions in which the absorbing substance is dissolved. Blood is a suspension, and, consequently, the relationship between $SaO_2$ and the ratio of the optical density for red and infrared radiation is nonlinear, as shown in FIG. 8. Between 30% and 60% saturation, the relationship is almost linear; above this range the relationship is nonlinear. The curve in FIG. 8 is an example of a suitable calibration curve which may be programmed into the microprocessor, e.g., in the form of a lookup table, for calculation of $SaO_2$. Further information regarding methods of measuring blood oxygen saturation may be found in the following references which are hereby incorporated by reference: Geddes, "Heritage of the Tissue-Bed Oximeter," *IEEE Engineering in Medicine and Biology*, 87–91, March/April 1997; Geddes and Baker, *Principles of Applied Biomedical Instrumentation*, $3^{rd}$ ed., Wiley, New York, 1989.

Calibration of the oximeter also involves balancing the outputs for the red and infrared channels to obtain the same optical sensitivity for both, and ensuring that both channels have a linear response to the red and infrared radiation.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, although the embodiment of FIG. 2 is described above as having two emitters and one detector, it may instead be provided with one emitter and two detectors or with a combination of multiple emitters and multiple detectors. The emitter(s) and detector(s) may be mounted inside the cuff, on the inside surface of the cuff's inner wall, that is, the wall which contacts the subject's skin during use, and may be affixed thereto with an optically clear adhesive, e.g., Superglue or other adhesive suitable for the particular material used for the cuff. The emitter(s) and detector(s) may be affixed to the cuff wall before the cuff is completely formed or sealed, and the cuff may then be sealed so as to enclose the emitter(s)

and detector(s). The system may also be provided with an alarm which is triggered when the transducer is off the body member desired to be monitored; an alarm circuit may be designed to respond, for example, to an optical sensor output signal level that is beyond a predetermined threshold, indicative of the absence of absorbing material in the optical path, or to such a condition combined with the additional condition of an absence of optical pulses.

We claim:

1. An oscillometric, noninvasive blood pressure monitor, comprising:
   an inflatable cuff;
   a pump connected to said cuff;
   a pressure transducer connected to said cuff, said pressure transducer producing a cuff-pressure signal;
   means for detecting oscillations in arterial pressure occurring during a transition in cuff pressure between a pressure greater than normal systolic pressure and a pressure less than normal diastolic pressure; and
   a blood pressure measurement circuit responsive to said oscillations, said circuit determining the maximum amplitude $A_m$ of said oscillations, identifying mean cuff pressure $P_m$ as the coincident value of said cuff-pressure signal, and determining systolic pressure as a function of both $A_m$ and $P_m$.

2. The blood pressure monitor of claim 1, further comprising an optical sensor including a light source and photodetector,
   wherein said detecting means detects said arterial pressure oscillations as oscillations in the output signal of said photodetector, and wherein said blood pressure measurement circuit determines the oscillation amplitude $A_s$ corresponding to systolic pressure as a function of both $A_m$ and $P_m$.

3. The blood pressure monitor of claim 2, wherein said blood pressure measurement circuit determines the amplitude $A_s$ corresponding to systolic pressure based on an equation of the form $$A_s = A_m(a - b\, P_m)$$

where a and b are constants.

4. The blood pressure monitor of claim 3, wherein the value a is greater than 0.7, and the value b is greater than 0.001 for $P_m$ in units of mm Hg.

5. The blood pressure monitor of claim 4, wherein the value a is approximately 0.84 and the value b is approximately 0.004.

6. The blood pressure monitor of claim 1, wherein said detecting means is coupled to said pressure transducer and detects said arterial pressure oscillations as oscillations in said cuff-pressure signal, and wherein said blood pressure measurement circuit determines the oscillation amplitude $A_s$ corresponding to systolic pressure as a function of both $A_m$ and $P_m$.

7. The blood pressure monitor of claim 6, wherein said blood pressure measurement circuit determines the amplitude $A_s$ corresponding to systolic pressure based on an equation of the form $$A_s = A_m(a - b\, P_m)$$

where a and b are constants.

8. The blood pressure monitor of claim 7, wherein the value a is greater than 0.7, and the value b is greater than 0.001 for $P_m$ in units of mm Hg.

9. The blood pressure monitor of claim 8, wherein the value a is approximately 0.84 and the value b is approximately 0.004.

10. An oscillometric, noninvasive method of measuring blood pressure, comprising:
    inflating a cuff,
    producing a cuff-pressure signal with a pressure transducer connected to said cuff;
    detecting oscillations in arterial pressure occurring during a transition in cuff pressure between a pressure greater than normal systolic pressure and a pressure less than normal diastolic pressure;
    determining the maximum amplitude $A_m$ of said oscillations;
    identifying mean cuff pressure $P_m$ as the value of said cuff-pressure signal coinciding in time with $A_m$; and
    determining systolic pressure as a function of both $A_m$ and $P_m$.

11. The method of claim 10, wherein said arterial pressure oscillations are detected as oscillations in the output signal of an optical sensor, said method further comprising:
    determining the oscillation amplitude $A_s$ corresponding to systolic pressure as a function of both $A_m$ and $P_m$.

12. The method of claim 11, wherein the amplitude A, corresponding to systolic pressure is determined based on an equation of the form $$A_s = A_m(a - b\, P_m)$$

where a and b are constants.

13. The method of claim 12, wherein the value a is greater than 0.7, and the value b is greater than 0.001 for $P_m$ in units of mm Hg.

14. The method of claim 13, wherein the value a is approximately 0.84 and the value b is approximately 0.004.

15. The method of claim 10, wherein said arterial pressure oscillations are determined as oscillations in said cuff-pressure signal, said method further comprising:
    determining the oscillation amplitude $A_s$ corresponding to systolic pressure as a function of both $A_m$ and $P_m$.

16. The method of claim 15, wherein the amplitude $A_s$ corresponding to systolic pressure is determined based on an equation of the form $$A_s = A_m(a - b\, P_m)$$

where a and b are constants.

17. The method of claim 16, wherein the value a is greater than 0.7, and the value b is greater than 0.001 for $P_m$ in units of mm Hg.

18. The method of claim 17, wherein the value a is approximately 0.84 and the value b is approximately 0.004.

* * * * *

UNITED STATES PATENT AND TRADEMARK OFFICE
CERTIFICATE OF CORRECTION

| | | |
|---|---|---|
| PATENT NO. | : 7,014,611 B1 | Page 1 of 1 |
| APPLICATION NO. | : 10/876308 | |
| DATED | : March 21, 2006 | |
| INVENTOR(S) | : Leslie A. Geddes and Rebecca A. Roeder | |

It is certified that error appears in the above-identified patent and that said Letters Patent is hereby corrected as shown below:

In column 8, line 29, please change "A," to --$A_s$--.

Signed and Sealed this

Eighth Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,014,611 B1 | Page 1 of 1 |
| APPLICATION NO. | : 10/876308 | |
| DATED | : March 21, 2006 | |
| INVENTOR(S) | : Leslie A. Geddes et al. | |

It is certified that error appears in the above-identified patent and that said Letters Patent is hereby corrected as shown below:

Col. 1, Line 5, Insert:
--GOVERNMENT RIGHTS
This invention was made with government support under Grant No. #5 R21 EB001540-03 awarded by the National Institutes of Health. The government has certain rights in the invention.--

Signed and Sealed this

First Day of July, 2008

JON W. DUDAS
*Director of the United States Patent and Trademark Office*